United States Patent [19]

Garman

[11] Patent Number: 6,054,282
[45] Date of Patent: *Apr. 25, 2000

[54] METHOD FOR DETECTING BIOLOGICAL INTERACTIONS ESPECIALLY IN RECEPTOR BINDING ASSAYS

[75] Inventor: Andrew John Garman, Ashton, United Kingdom

[73] Assignee: Zeneca Limited, London, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/596,210

[22] PCT Filed: Aug. 17, 1994

[86] PCT No.: PCT/GB94/01799

§ 371 Date: Feb. 14, 1996

§ 102(e) Date: Feb. 14, 1996

[87] PCT Pub. No.: WO95/05601

PCT Pub. Date: Feb. 23, 1995

[30] Foreign Application Priority Data

Aug. 18, 1993 [GB] United Kingdom .................. 9317193

[51] Int. Cl.[7] ...................... G01N 33/558; G01N 33/566; G01N 33/567
[52] U.S. Cl. .......................... 435/7.2; 435/7.8; 435/7.93; 436/501; 436/503; 436/504; 436/514; 436/518
[58] Field of Search .......................... 435/7.2, 7.8, 7.93; 436/501, 503, 514, 518, 504

[56] References Cited

U.S. PATENT DOCUMENTS

| | | | |
|---|---|---|---|
| 3,645,687 | 2/1972 | Nerenberg | 436/514 |
| 4,517,285 | 5/1985 | Giegel et al. | 435/7 |
| 4,666,863 | 5/1987 | Edwards et al. | 436/514 |
| 4,670,381 | 6/1987 | Frickey et al. | 435/7 |
| 4,752,562 | 6/1988 | Sheiman et al. | 435/5 |
| 5,264,372 | 11/1993 | Beaumont et al. | 436/504 |

FOREIGN PATENT DOCUMENTS

| | | |
|---|---|---|
| 120 602 | 10/1984 | European Pat. Off. . |
| 0 267 006 | 5/1988 | European Pat. Off. . |
| 488 170 | 6/1992 | European Pat. Off. . |
| 0 553 773 | 8/1993 | European Pat. Off. . |
| 2 232 486 | 12/1990 | United Kingdom . |
| 93 14403 | 7/1993 | WIPO . |
| 93 14408 | 7/1993 | WIPO . |

OTHER PUBLICATIONS

Giegel, et al: "Radial partition immunoassay", Clinical Chemistry, vol. 28, No. 9, Sep. 1982, pp. 1894–1898.

Search Report for application No. GB 9416583.4, UK Patent Office (citing above documents not already of record.).

*Primary Examiner*—David Saunders
*Attorney, Agent, or Firm*—Pillsbury Madison & Sutro, LLP Intellectual Property Group

[57] ABSTRACT

A method for the detection of a compound which modulates binding of a ligand to a biological receptor, which method comprises contacting the ligand, biological receptor and test compound at a locus on a solid phase matrix, the matrix allowing movement of fluids therein by capillary action, under conditions which permit binding of the ligand to the biological receptor and partition of any unbound ligand on the solid phase matrix, and detecting any modulation of binding by the test compound by reference to any such partition.

10 Claims, 4 Drawing Sheets

METHOD FOR DETECTING BIOLOGICAL INTERACTIONS ESPECIALLY IN RECEPTOR BINDING ASSAYS

This application claims benefit of international application PCT/GB94/01799, filed Aug. 17, 1994.

The present invention relates to improved methods of detecting biological interactions especially in receptor binding assays. In particular the invention involves the use of radial partition.

Conventional radioligand binding assays are involved, ie. they employ vacuum filtration and other complex procedures. Such procedures are outlined for example in Receptor-Ligand Interactions, E. D. Hulme (Ed), 1992, IRL Press. A need therefore exists for further improved techniques which are less cumbersome to perform and more suitable, for example, for the identification of new drug leads by high throughput screening.

Radial partition was first described as long ago as 1982 (J. L. Giegel et al, Clin. Chem., 28, 1894–1898(1982)). Since then it has become well established as the basis for assays in the immunodiagnostics field. A typical method employs an antibody immobilised on a paper filter with sequential application of analyte and second antibody conjugate. A wash (optionally containing substrate for enzyme immunoassays) is then applied such that unbound conjugate is washed radially away from the centre leaving bound conjugate as a central dot. Quantitation according to the signal used gives, by reference to a standard curve, the concentration of the analyte.

We have now surprisingly found that the principle of radial partition may be successfully applied in novel assays for the identification of compounds which bind to a biological receptor of interest. Such novel partition assays do not require vacuum filtration or other complex procedures. These may be readily applied in rapid or high throughput screening procedures, and used for the identification of novel active compounds in, for example, the pharmaceutical and agrochemical industries.

Therefore according to a first aspect of the present invention we provide a method for the detection of a compound which modulates binding of a ligand to a biological receptor, which method comprises contacting the ligand, biological receptor and test compound at a locus on a solid phase matrix, the matrix allowing movement of fluids therein by capillary action, under conditions which permit binding of the ligand to the biological receptor and partition of any unbound ligand on the solid phase matrix, and detecting any modulation of binding by the test compound by reference to any such partition.

Components of the above assay may be added to the matrix in any order. optionally three, preferably two of the components may be mixed prior to application to the matrix. Preferably, the order should be such that the ligand does not contact the biological receptor before the test compounds, since this would require any active compound to displace the ligand and this might be kinetically slow and reduce the sensitivity of the assay. Preferably the first addition should contain the biological receptor. Preferably the biological receptor is immobilised on the solid phase matrix.

Alternatively the method of the invention may be used to determine interactions between a biological receptor of interest and a test compound. Therefore in a further aspect of the present invention we provide a method for the detection of a compound which binds to a biological receptor, which method comprises contacting the biological receptor with a test compound at a locus on a solid phase matrix, the matrix allowing movement of fluids therein by capillary action, under conditions which permit binding of the test compound to the biological receptor and partition of any unbound test compound on the solid phase matrix, and detecting binding of the test compound to the biological receptor by reference to any such partition.

Conveniently the test compound is immobilised on the solid phase matrix prior to application of the other assay component.

By "immobilised" we mean covalent or non-covalent attachment to the matrix, or attachment to a substance which is unable to migrate through the matrix by capillary action. In the case where the receptor is a membrane receptor, immobilisation is conveniently provided by application of the receptor in the form of membrane fragments. Alternatively the receptor may be provided with a peptide tag, conveniently attached to the N- or C-terminus and produced as a fusion product by genetic manipulation technology, and immobilisation effected by means of a partner complementary to the tag, for example an anti-tag antibody, immobilised on the matrix by covalent or non-covalent means. Where the test compound is immobilised, this is conveniently achieved by synthesis of the test compound on the matrix. Such systems have been described for example by R. Frank, Tet. Lett. 48, (42), 9217–9232 (1992).

Whilst we do not wish to be bound by theoretical considerations, binding of the biological receptor to the test compound will generally take place in solution. Thus one or more of the relevant components are conveniently applied in solution.

Optionally drying or partial drying, for example by allowing a pause between additions may be employed in order to reduce the fluid volume of the assay.

A preferred assay comprises addition of the biological receptor, drying, addition of the test compound and then the ligand, incubation followed by washing.

Depending on the nature of the fluid medium and the solid phase matrix, after binding partition may have already taken place to some limited extent. However, in general, it is preferred to limit incubation to a defined locus and, after incubation, a wash fluid is then conveniently applied as a separate step to allow any desired degree of partition to occur.

The matrix of the present invention is conveniently a porous solid-phase matrix such as a sheet of cellulose paper or glass fibre paper or papers of mixed glass fibre and cellulose.

The partition of the present invention is conveniently radial partition followed by quantitation or estimation of the extent of the labelled component retained in the central locus or in the peripheral areas of the matrix, or both.

Alternatively the assay method is performed as a linear partition assay which permits a higher density of assay loci than outlined above. This assay is performed as described above but employs smaller volumes and/or thicker matrix eg. paper, such that a high proportion of the wash buffer is directed downwards (assuming a horizontal paper), this process optionally being facilitated by positioning the loci close together such that radial movement is restricted. Optionally this process may be facilitated by the provision of an adsorbent layer under the matrix. This assay is conveniently performed with the ligand labelled with a signal that cannot be detected significantly through the (opacue) paper, for example a chromophore, fluorophore, chemilumophore (or enzymes generating these) or tritium. Preferably the signal is a fluorophore. The extent of binding is determined by measuring the surface signal: thus compounds binding to the receptor will prevent binding of the labelled ligand and a diminished signal will result.

Both radial and linear assays may be carried out on any convenient two- or three-dimensional matrix including those where the structural integrity of the matrix is assisted by supporting surfaces. Convenient two-dimensional matrices include sheets of paper and the like, but it will be understood that they may be on separate supports, for example filters attached to the bottom of microtitre plates. The linear and radial partition assay may be performed on any matrix that allows the linear flow of the liquid.

The biological receptor is conveniently a pharmacological receptor of interest, such as a membrane receptor, or any target of for example pharmaceutical or agrochemical interest. Such targets may be for example proteins such as those involved in the mediation of cellular signalling, control of gene expression, cell adhesion, inflammation; enzymes and their inhibitors, proteoglycans, oligo- or poly-saccharides, nucleic acid in double or single stranded form, and complexes comprising one or more of the above species.

The biological receptor is conveniently provided in the form of membrane fragments. The biological receptor may be a fragment or domain or an analogue of the natural biological receptor of interest.

The ligand is conveniently selected from those compounds known to bind to the biological receptor of interest. Typically, the ligand may be a peptide, protein, oligo- or poly-saccharide, or a small molecule. The ligand may be an analogue of the naturally occuring ligand.

The methods of the invention are preferably carried out with with reference to one or more controls.

Detecting the presence of bound or unbound material is conveniently effected by labelling one or more of the soluble components of the particular system. Most conveniently the ligand is labelled. Alternatively the biological partner is labelled.

The label used may be any conventional label used in biochemical assays. For radial partition assays, the label is conveniently such that it may be be located and determined by a two-dimensional imaging technique, for example radioactivity that may be determined by autoradiography or storage phosphor or proportional wire counting or microchannel array detector technology, or fluorescence that may be determined by a fluorescence scanner device, or a colour, or enzyme-generated colour, that may be assessed by visual inspection or image analysis.

Alternative labelling and detection systems may be devised which obviate the need for the detection technique to distinguish between bound and free label. For example if fluorescence is employed as the label, only the centre of the locus may be illuminated, such that only the bound label fluoresces. Alternatively, if a radioisotope is employed as the label, after the assay a small volume of scintillant may be applied to the central portion of the locus only, such that only bound label will be detected. Alternatively, if an enzyme is employed as the label, after the assay a small volume of substrate may be applied to the central portion of the locus only, such that only bound label is detected. This principle may be applied to any signal system which requires two or more components to give the signal (including light irradiation as a component) and variations on the above will be apparent to the scientist of average skill.

For linear partition assays, the label is conveniently a fluorophore, or an enzyme that generates a signal that does not penetrate significantly the chosen matrix. Alternatively, weakly penetrating radioactive isotopes, such as tritium, may be employed.

Alternatively, for both radial and linear partition assays, interacting signals-may be employed, such that the bound or the free label is determined by an interaction with a second signal component located on the immobilised component or on the matrix. Interacting signals are known in the art and include for example fluorescence energy transfer. An intrinsic property of the immobilised partner or the matrix, for example its mass or its hydropathy, may be considered as an interacting signal, permitting detection by fluorescence polarisation or modulation of other fluorescence properties.

It will be understood that the term "label" includes tags that form one half of an affinity pair, such as biotin, whose presence may be subsequently determined by incubation with the complementary partner of the affinity pair to which has been conjugated a signal.

Methods for labelling ligands and biological partners are known in the art and are described for example in the catalogues of the Pierce Chemical Company and of Molecular Probes, and references contained therein.

We have found that radioligand binding assays can advantageously be performed in this form. The method comprises the steps of adding to a suitable paper, for example glass fibre paper, membrane fragments containing the receptor of interest, test compound and labelled ligand, preferably in that order and in a small volume, conveniently totalling less than 10 $\mu$l, such as less than 6 $\mu$l, and incubating under conditions to allow binding to occur. All additions are made at the same position on the paper. Subsequently, wash buffer of a convenient volume is applied, such that unbound ligand is washed radially while bound ligand remains in the centre, since the membrane fragments are unable to migrate through the paper.

Conveniently the ligand is labelled with a radioactive isotope and the assay result visualised by autoradiography, proportional wire counting, microchannel array detector or storage phosphor technology. The latter three techniques permit quantitation of the results. Alternatively, non-isotopic labels may be used, in particular fluorescent labels used in conjunction with two-dimensional fluorescence scanners are-convenient. In these approaches a test compound that prevents binding of the ligand to the receptor is revealed by a diminution in the intensity of the central spot.

We also disclose pre-treated membranes for use as a solid phase matrix in the above methods. Such membranes may be treated or coated with substances for example to improve non-specific binding of the labelled component to the matrix, or to retain the immobilised component in the central locus.

An advantage of the assay of the invention is that a plurality of assays may be conveniently carried out on a single sheet of matrix. Thus, a large number of compounds may be screened in a single experiment. Conveniently, this is achieved my means of robtic liquid handling devices. Several such devices are known and include for example robotic sample processors such as the Tecan RSP 5072.

The above assays give significant advantages over conventional techniques. These include increased throughput capacity, simpler operation, increased robustness and lower cost. For receptor binding assays using membrane fragments, it is also believed that the assay is more discriminating in its ability to detect compounds with genuine receptor binding activity. Whilst we do not wish to be bound by theoretical considerations, the more gentle filtration employed by this method, compared to vacuum filtration methods, results in compounds that merely disrupt the structure of the membrane fragments not being detected since the fragments, though disrupted, nevertheless remain in the central zone.

The invention will now be described but not limited with reference to the following Examples and Figures wherein.

EXAMPLE 1

Figure 1:
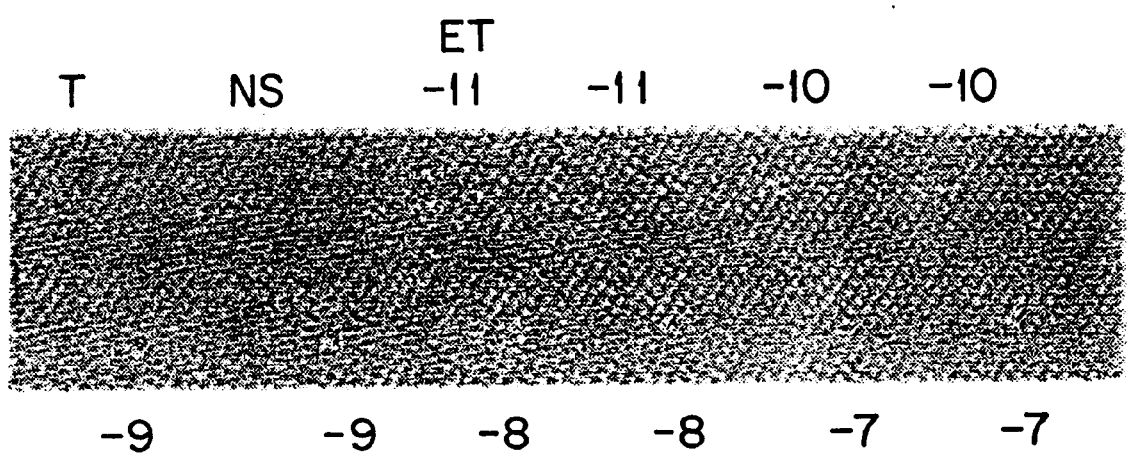
FIG. 1 shows an autoradiograph showing displacement of radiolabelled endothelin by different concentrations of unlabelled endothelin according to the assay described in Example 1. T: total (no unlabelled endothelin), NS: non-specific binding;-11,-10,-9,-8,-7: $10^{-11}$M, $10^{-10}$M, $10^{-9}$M, $10^{-8}$M and $10^{-7}$M unlabelled endothelin.

Establishment of an Endothelin Receptor Rinding Assay

This assay investigates the interaction of endothelin 1 with a washed membrane fraction prepared from mouse erythroleukaemia (MEL) cells expressing the human endothelin $ET_A$ receptor (ET receptor—Adachi et al, Biochem. Biophys. Res. Commun., 1991, 180, 1265–1272), separated in a radial format.

A fresh pellet of MEL cells (WO-89/01117-Grosveld et al/MRC, WO-92/11380-Hollis et al/ICI) containing the cloned human $ET_A$ receptor was obtained. These cells were re-suspended in homogenisation buffer (50 mM Tris [hydroxymethyl]amino- methane (Trizma base), 5 μg/ml soybean trypsin inhibitor, 1 mM 1,10-phenanthroline, 1 mM benzamidine hydrochloride, 100 μg/ml bacitracin, (all from Sigma), 3 mM sucrose (BDH); pH 8.0 with HCl). The cell suspension was homogenised using a mechanical homogeniser (Polytron PT-3000 on 75% power) for 3×10 second bursts with 2 minutes cooling on ice in-between bursts. The homogenate was centrifuged at 1500×g for 10 minutes at 4° C. (SS34 rotor—Sorval RC5C centrifuge). The supernatant was poured off and re-centrifuged at >40,000×g for 30 minutes at 4° C. (SS34 rotor—Sorval centrifuge). The resulting supernatant was discarded and the pellet washed by re-suspending in homogenisation buffer (as previously described) and re-centrifuging at >40,000×g for 30 minutes (as above). The final pellet was re-suspended in homogenisation buffer using a glass/Teflon hand held homogeniser. Aliquots of the final membrane suspension were stored frozen in liquid nitrogen until required.

All assay dilutions were made using assay buffer (50 mM Trizma base, 1 mM CaCl2, 0.05% polyoxyethylenesorbitan monolaurate (Tween 20, Sigma), 0.1% bovine serum albumin (fatty acid free); heat treated to 56° C. for 30 minutes, pH7.4). A stock solution of endothelin 1 (human, porcine, Cambridge Research Biochemicals) was prepared at $3\times10^7$ M in de-ionised water and stored in aliquots at −20° C. until needed. The stock solution was diluted with assay buffer (as above) to give a concentration of $3\times10^-$ M, this concentration was used to define the non-specific binding. Dilutions of this were made to give a range of concentrations from $3\times10^{-7}$M to $3\times10^{-1}$M. The freshly thawed membrane suspension was diluted to give about 0.3 mg/ml protein concentration, 15 μl of which was applied to all assay positions on a glass fibre filter mat (Whatman GFB). This was allowed to partially dry at room temperature for 20 minutes. 15 μl of either assay buffer (to give total binding), or a dilutions of endothelin 1 were applied to the membrane spots, immediately followed by 15 μl of 90 pM (0.2 terabecquerels/mmol) [125I]-Tyr13-endothelin 1 l(human, porcine, NEN Research Products) were applied to the same spots. The mat was then incubated in a humid atmosphere at 37° C. for 40 minutes, after which time 60 μl of wash buffer (50 M Tris-HCl, pH7.4) was applied to the same spots. The mat was then exposed to autoradiography film (Fuji X-ray) for 3 days.

The results are given in FIG. 1. The radioactivity bound to the membranes did not move, whilst the unbound radioactivity was washed out from the central spot in a radial manner, forming an outer circle. FIG. 1 shows a central spot for the total binding (T) and an absence of a spot for the non-specific binding (10–7M endothelin). The four dilutions of endothelin show a progressive loss of the central spot consistent with an IC-50 of between 10–10 and 10–11M.

EXAMPLE 2

Detection of the Activity of Test Compounds and Correlation With Conventional Methodology 24 compounds of known activity in a conventional endothelin receptor binding assay were selected for this experiment. In brief, the conventional assay employed incubation of the membrane receptor fragments and radiolabelled endothelin (as described in Example 1) with test compounds. After incubation for 90 minutes, the mixture was filtered through a glass fibre mat (Wallac printed filter mat B) using vacuum filtration on a cell harvester (Tomtec 96 Mach 2), and counted on a beta counter (Wallac 1205 BetaPlate). The percentage displacement for each compound was calculated by reference to the total and non-specific binding controls.

These compounds were assayed at a final concentration 0.3 mM in the radial partition assay as described in Example 1, with the following modifications: the volumes of receptor, compound and label were 2, 4 and 4 microlitres respectively and the wash volume was 5 microlitres. The filter employed was a reinforced mat (Tomtec RG).

The mat was exposed to a storage phosphor screen (Molecular Dynamics) for 3 hours and analysed on a PhosphorImager SF (Molecular Dynamics). The intensity of the central spots was determined using the software provided. The displacement for each compound was calculated by subtracting the non-specific binding value from all values and expressing total counts—compound counts as a percentage of total counts.

Figure 2:
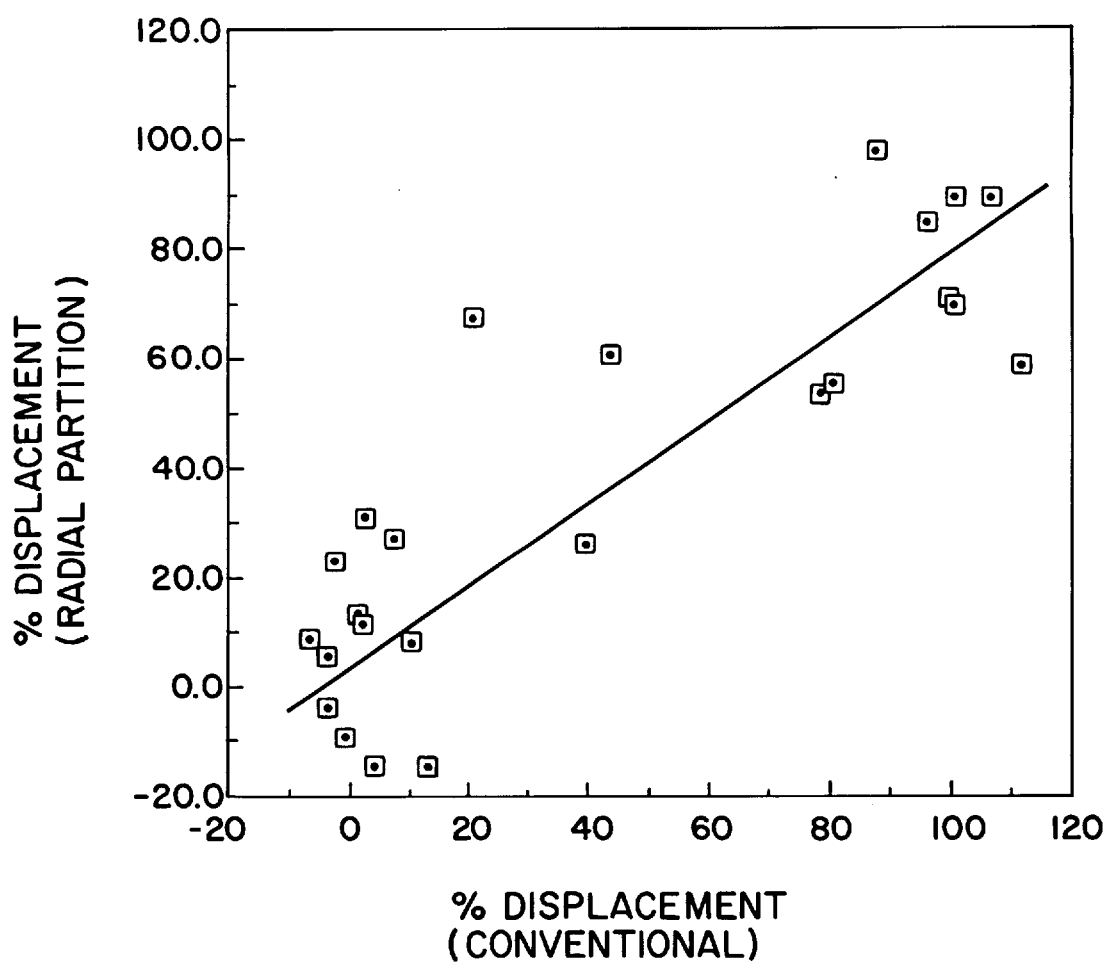
FIG. 2 shows the correlation in the percentage displacement obtained for 24 test compounds in the radial partition assay as described in Example 2 against the conventional vacuum filtration method.

The displacement for the compounds for this assay are compared with those obtained in the conventional assay in FIG. 2. The high degree of correlation shows that the assay of the invention is useful in detecting compounds which inhibit the binding of a ligand with a receptor.

EXAMPLE 3

Multiple Assays Using Human Calcitonin Receptor

Recombinant human calcitonin receptor preparations were obtained as follows: a fresh pellet of MEL cells (WO-89/01517-Grosveld et al/MRC, WO-92/11380-Hollis et al/ICI) containing the cloned human calcitonin receptor (cf. Gorn, A. H. et al J. Clin. Invest., (1992), 90, 1726–1735) was re-suspended in cold (4 deg.C.) homogenisation buffer (20 mM HEPES, 100 mM NaCl, 5 mM EDTA, 0.1 mM phenylmethylsulfonyl fluoride (PMSF), 1 mM iodoactamide, pH 7.4). The cell suspension was homogenised using a mechanical homogeniser (Polytron PT-3000 on 75% power) for 3×10 second bursts with 2 minutes cooling on ice between bursts. The lysate was transferred to a glass/Teflon homogeniser and given 10 strokes to ensure cell disruption. The homogenate was centrifuged at 3,000 rpm (1100 g) for 10 minutes at 4 deg.C. (SS34 rotor-Sorval RC5C centrifuge). The low-speed supernatant was removed, and the pellet re-suspended in 10 ml of homogenisation buffer and dispersed with 3×10 second treatments with the Polytron homogeniser, followed by low-speed centifugation as described above. The supernatants from both spins were combined. This was then centrifuged for 30 minutes at 33,000 rpm (100,000 g) at 4 deg C. in an L7 Ultracentrifuge (Beckman) using a Ti75 head. The pellet was re-suspended in 20 mM HEPES, pH 7.4, and re-centrifuged. This pellet was then re-suspended as before and treated with 10 strokes of the glass/Teflon homogeniser.

Protein determination was by the ECA method of the Pierce Chemical Co., using their recommended protocol and bovine serum albumin (BSA) as a standard. Membranes were diluted to a stock concentration of 0.08 mg/ml protein, and stored at −70 deg. C.

All assay dilutions were made using assay buffer (20 mM HEPES, 120 mM NaCl, 0.25% BSA (fatty acid free), 0.1% bacitracin, pH 7.4. A stock solution of calcitonin (salmon, Cambridge Research Biochemicals) was prepared at 0.1 mM in 100 mM sodium phosphate buffer, containing 150 mM NaCl and 0.1% BSA, pH 7.5, and a dilution in assay buffer at 0.3 nM prepared. A solution of (3-[125I]iodotyrosyl-22) salmon calcitonin (0.3 nM) was prepared and a portion mixed 1:1 with the unlabelled calcitonin to give an isotopically diluted preparation. The freshly thawed membrane suspension was diluted to a working concentration of 0.02 mg/ml.

To a 30×43 cm glass fibre filter mat (Tomtec RG) was added 4 microlitres of receptor preparation to 2,304 positions in a rectangular array. This was allowed to dry for 2 hours at room temperature. 2 microlitres of either assay buffer (to give total binding) or a dilution of salmon calcitonin were applied along with 2 microlitres of the 125I) salmon calcitonin in the same addition. Each assay position-was allowed to incubate at room temperature for 40 minutes, after which time 6 microlitres of wash buffer (10 mM Tris [hydroxymethyl]amino-methane (Trizma base) (Sigma), 150 mM sodium chloride (Fisons AR), pH7.4, with 0.05% polyoxyethylenesorbitan monolaurate (Sigma)), was applied. All additions were made using a Tecan RSP 5072 robotic sample processor with a 4 way tip.

The mat was allowed to dry completely and was exposed to a storage phosphor screen (Molecular Dynamics) for 3 hours and analysed using a PhosphorImager SF (Molecular Dynamics).

Figure 3:
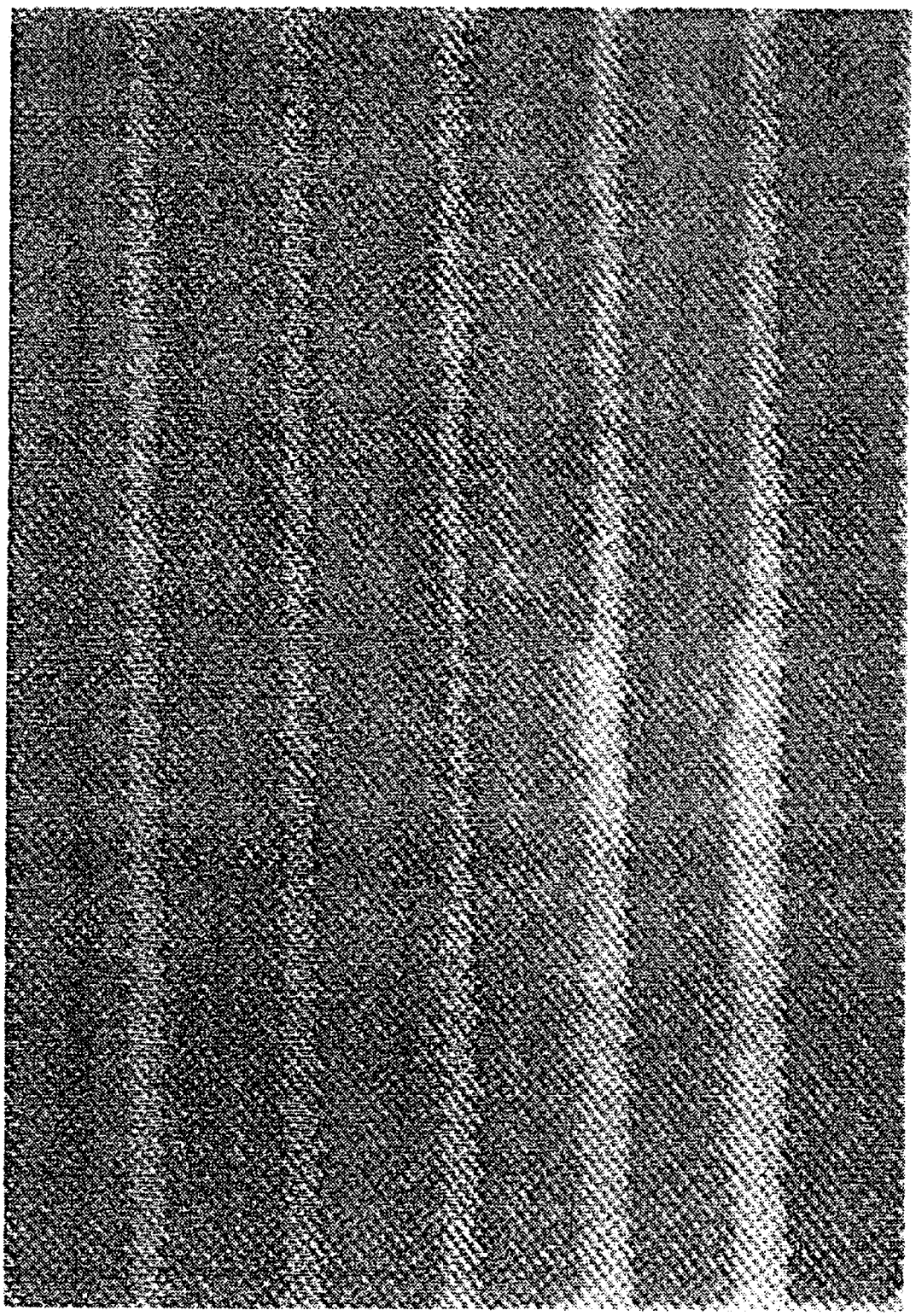
FIG. 3 shows the image obtained by following the procedures set out in Example 3. This shows dark central spots indicating total binding to the localised receptor,the absence of a spot indicates full inhibition of binding due to a high concentration of salmon calcitonin being applied to that position (1 micromolar).

The image obtained from the PhosphorImager is shown in FIG. 3. This shows the dark central spots indicating total binding to the localised receptor, the absence of a spot indicates full inhibition of binding due to a high concentration of salmon calcitonin being applied to that position (1 micromolar). Although the application of small volumes to a filter mat requires care the figure shows that the invention is a convenient way to increase greatly the number of tests possible in one simple assay.

EXAMPLE 4
Bradykinin Binding: Various Receptor Membrane Concentrations.

Recombinant human bradykinin receptor preparations were obtained as follows: a fresh pellet of MEL cells (WO-89/01517-Grosveld et al/MRC, WO-92/11380-Hollis et al/ICI) containing the cloned human bradykinin receptor was re-suspended in cold (4 deg. C.) homogenisation buffer (10 mM Tristhydroxymethyllamino-methane (Trizma base) pH 7.5, 0.1 mg/ml bacitracin, 0.005 mg/ml soybean trypsin inhibitor (5 mg/ml pre-solubilised in ethanol), 1 mM benzamidine, 250 mM phenylmethylsulfonylflouride (in ethanol) (all from Sigma), 0.2M sucrose (Fisons AR)). The cell suspension was homogenised (Ultra-turax at 20,500 rpm) for 3×10 second bursts with 2 minute cooling on ice between bursts. The lysate was centifuged at 3500 rpm (1500 g) for 10 minutes at 4 deg. C. (SS34 rotor—Sorval RC5C centrifuge). The low speed supernatant was removed and the pellet discarded. The supernatant was centrifuged for 30 minutes at 20,000 rpm (40000 g) at 4 deg. C. in the Sorval centrifuge.

Protein determination was by the BCA method of the Pierce Chemical Co., using their recommended protocol and BSA as a standard. Membranes were aliquoted and stored at −70 deg. C. until use.

Freshly thawed membrane solution was diluted in assay buffer (37.5 mM N-tris[Hydroxymethyl]m-methyl-2-aminoethane-sulphonic acid (TES), 1.5 mM phenanthroline, 0.21 mg/ml bacitracin, 0.15 mM thiorphan, 0.15% bovine serum albumin (essentially fatty acid free) (BSA) (all from Sigma), 0.45 mM magnesium chloride (BDH), pH 6.8, heat treated for 30 minutes at 56 deg. C.), to give five concentrations of membranes A. 0.7 mg/ml
B. 0.5 mg/ml
C. 0.3 mg/ml
D. 0.1 mg/ml
E. 0.05 mg/ml A solution of [125I-Tyr8]-bradykinin (NEN Research Products) was prepared in assay buffer to give a concentration of 0.15 pM. A stock solution of a standard bradykinin receptor antagonist (M248138) was prepared at a concentration of 0.3 mM and a dilution in Tris (hydroxymethyllamino-methane (Trizma base) (TRIS) (Sigma), pH 7.0 was made to give a concentration of 0.05 mM, this was used to determine the non-specific binding.

A glass fibre filter mat (Tomtec RG) was soaked in 0.15% polyethyleneimine (Sigma) at 4 deg. C. for 10 hours and left to dry completely. 4×4 microlitre spots of each membrane concentration were applied to the dry filter mat and left at room temperature for 2 hours. 2 microlitres of either TRIS buffer (to give total binding), or 2 microlitres of the inhibitor (to give non-specific binding) were applied to each spot, immediately followed by 2 microlitres of [125I]-bradykinin.

The mat was left at room temperature for 40 minutes, after which time 6 microlitres of wash buffer (1 mM TRIS, 100 mM sodium chloride (Fisons AR), 0.02% BSA pH 7.5) was applied to each spot. When dry the mat was exposed to a storage phosphor screen (Molecular Dynamics) for 3 hours and analysed on a PhosphoImager SF (Molecular Dynamics).

Figure 4:
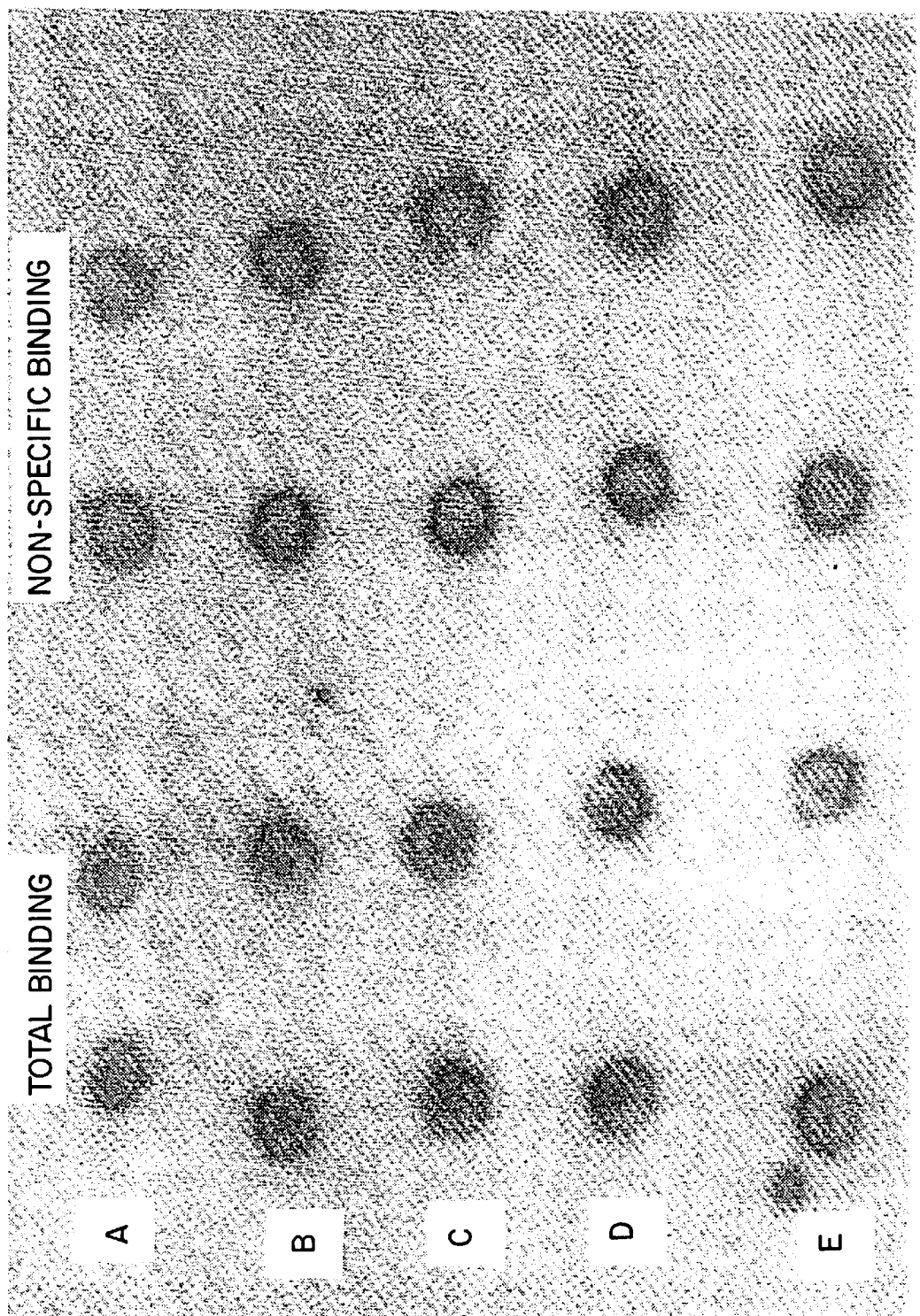
FIG. 4 shows the image obtained by following the procedures set out in Example 4. This shows the effects of total binding I and non-specific binding II as determined at the following membrane concentrations: A. 0.7 mg/ml, B. 0.5 mg/ml, C. 0.3 mg/ml, D. 0.1 mg/ml, E. 0.05 mg/ml.

The image obtained from the PhosphorImager is shown in FIG. 4. This shows that with each concentration total binding and non-specific binding can be determined and that as the concentration of membranes decreases the total binding decreases in a linear manner, confirming that the invention can be used with various different receptors and receptor concentrations.

I claim:
1. A method for the detection of a compound which modulates binding of a ligand to a membrane receptor, which method comprises contacting said ligand, membrane fragments comprising said receptor and a test compound at a locus on a solid phase matrix, said matrix allowing movement of fluids therein by capillary action, under conditions which permit binding of said ligand to said receptor in the absence of said test compound and which permit partitioning of any unbound ligand from any ligand bound to said receptor on the solid phase matrix, and detecting modulation of binding of said ligand to said receptor by the test compound by determining the extent of any partitioning of said ligand from said receptor.

2. A method as claimed in claim 2 wherein said ligand is labeled.

3. A method for the detection of a compound which binds to a membrane receptor, which method comprises contacting membrane fragments comprising said receptor with a test compound at a locus on a solid phase matrix, said matrix allowing movement of fluids therein by capillary action, under conditions which permit binding of said test compound to said receptor and partitioning of any unbound test compound from any test compound bound to said receptor on the solid phase matrix, and detecting binding of said test compound to said receptor by determining the extent of any partitioning of said test compound from said receptor.

4. A method as claimed in claim 1 or claim 3 wherein said partitioning is linear partitioning.

5. A method as claimed in claim 1 or claim 3 which is a radioligand binding assay.

6. A method as claimed in claim 1 or claim 3 wherein a plurality of test compounds is assayed on a single solid phase matrix.

7. The method as claimed in claim 3 wherein said test compound is labeled.

8. The method as claimed in claim 2 or claim 7 wherein the presence of label bound or unbound to said membrane receptor is detected using fluorescence.

9. The method as claimed in claim 2 or claim 7 wherein the presence of label bound or unbound to said membrane receptor is determined by interacting signals.

10. A solid phase matrix which matrix has been treated or coated with membrane fragments comprising a membrane receptor in the absence of any ligand for said receptor, said matrix allowing movement of fluids therein by capillary action, under conditions which permit binding of a ligand to said receptor on said matrix.

* * * * *